US008083966B2

(12) United States Patent
Thonhauser et al.

(10) Patent No.: US 8,083,966 B2
(45) Date of Patent: Dec. 27, 2011

(54) CLEANING DISINFECTION AND INDICATOR AGENT

(75) Inventors: Philip Thonhauser, Perchtoldsdorf (AT); Christian Thonhauser, Vienna (AT)

(73) Assignee: Thonhauser GmbH, Perchtoldsdorf (AT)

( * ) Notice: Subject to any disclaimer, the term of this patent is extended or adjusted under 35 U.S.C. 154(b) by 1084 days.

(21) Appl. No.: 10/578,593

(22) PCT Filed: Nov. 9, 2004

(86) PCT No.: PCT/AT2004/000392
§ 371 (c)(1),
(2), (4) Date: May 8, 2006

(87) PCT Pub. No.: WO2005/044968
PCT Pub. Date: May 19, 2005

(65) Prior Publication Data
US 2007/0102665 A1    May 10, 2007

(30) Foreign Application Priority Data

Nov. 11, 2003  (AT) .................... A 1817/2003

(51) Int. Cl.
| | |
|---|---|
| *A62D 3/00* | (2007.01) |
| *A62D 9/00* | (2006.01) |
| *C01B 7/00* | (2006.01) |
| *C01B 11/00* | (2006.01) |
| *C02F 1/00* | (2006.01) |
| *C09K 3/00* | (2006.01) |
| *C11D 3/39* | (2006.01) |

(52) U.S. Cl. ........... 252/186.1; 252/186.21; 252/186.25; 252/186.26; 252/186.27; 252/186.3

(58) Field of Classification Search ........................ None
See application file for complete search history.

(56) References Cited

U.S. PATENT DOCUMENTS

| | | | | |
|---|---|---|---|---|
| 5,747,794 A * | 5/1998 | Malchesky | ............... | 250/227.23 |
| 2003/0151024 A1* | 8/2003 | Wegner | ..................... | 252/186.28 |
| 2004/0213750 A1* | 10/2004 | Bennett et al. | ............... | 424/70.1 |

FOREIGN PATENT DOCUMENTS

SE    508 954    11/1998

OTHER PUBLICATIONS

Derwent-acc-No. 1994-037035, FR 2692881A1.*

(Continued)

*Primary Examiner* — Duy Deo
(74) *Attorney, Agent, or Firm* — Pillsbury Winthrop Shaw Pittman LLP

(57) ABSTRACT

A cleaning, disinfection, and indicator agent comprising a water-soluble permanganate, particularly for mixture with an agent for ensuring an alkaline milieu having a pH value of at least 11, which, in addition to the water-soluble permanganate, contains a further oxidizing agent, whose oxidation potential is above that of manganese VII to manganese VI, pH buffer substances, preferably primary and/or secondary alkali carbonates such as sodium carbonate and/or sodium hydrogen carbonate, as well as oxidation-resistant polyphosphates. Furthermore, methods for cleaning, disinfecting, and monitoring the cleanliness of commercial and industrial plants or plant components and the use of an agent according to the present invention as an indicator solution for ascertaining the cleanliness of commercial and industrial plants or plant components by ascertaining the intensity of the light emitted in the violet wavelength range by the solution are described.

42 Claims, 1 Drawing Sheet

OTHER PUBLICATIONS

Derwent-acc-No. 2003-037710, RU 2191163C1.*
AT 408 987 B, Apr. 2002, Austria (ISR) (w/English Abstract).
JP 61 192748 A, Aug. 1986, Japan (Abstract Only) (ISR).
WO 98/42812 A, Oct. 1998, PCT (ISR).
WO 03/035812 A, May 2003, PCT (ISR).
International Search Report.
Dipling. *Thonhauser GmbH* vs. *Norden Olje Aps*, Case No. FS9398/2009, Declaration by Mr. Wilfred Paul Worsley.
Dipling. *Thonhauser GmbH* vs. *Norden Olje Aps*, Case No. FS9398/2009, Respondents Statement of Defense.

* cited by examiner

Fig. 1: Relative Stability (50% / 50%)
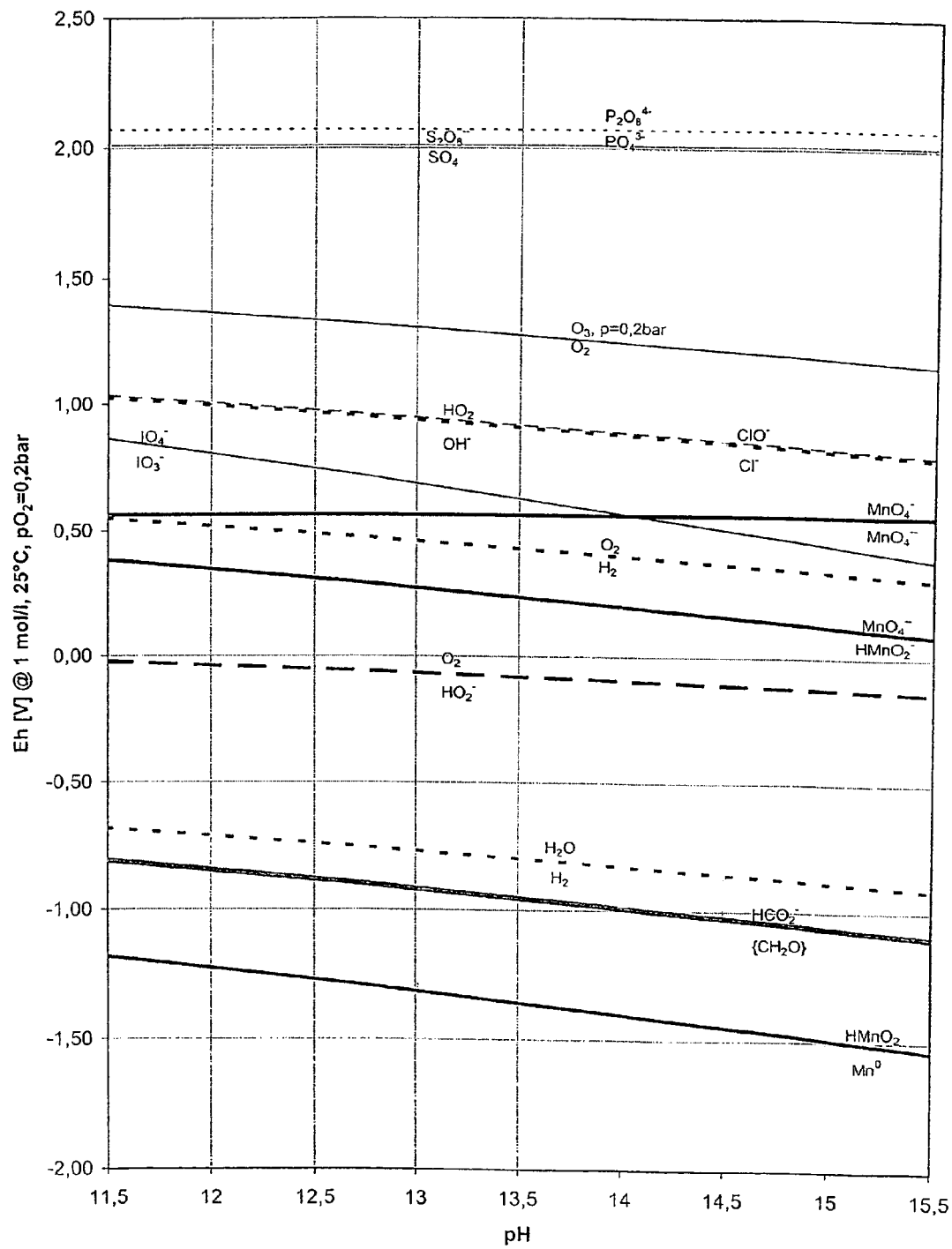

CLEANING DISINFECTION AND INDICATOR AGENT

CROSS REFERENCE TO RELATED APPLICATIONS

Applicant claims priority under 35 U.S.C. §119 of Austrian Application No. A 1817/2003 filed Nov. 11, 2003. Applicant also claims priority under 35 U.S.C. §365 of PCT/AT2004/000392 filed Nov. 9, 2004. The international application under PCT article 21(2) was not published in English.

The present invention relates to a cleaning, disinfection, and indicator agent according to the preamble of claim 1, a method for cleaning, disinfecting, and monitoring the cleanliness of commercial and industrial plants or plant components according to claims 9 and 11, and the use of a solution of a cleaning, disinfection, and indicator agent according to the present invention according to claim 16.

A cleaning and disinfection agent containing a water-soluble permanganate, in particular potassium permanganate ($KMnO_4$), as well as a further oxidizing agent, whose potential is above that of manganese VII to manganese VI, preferably above that of $HO_2^-$ to $OH^-$, was disclosed in AT 408987. As noted therein, potassium permanganate is a strong oxidizing agent whose bactericidal effect has been known for some time. In the strongly alkaline milieu, it is based above all on the reduction of the heptavalent manganese to the oxidation state +6. However, a use in cleaning and disinfection agent is problematic for different reasons. Thus, potassium permanganate has been shown to be poorly compatible with other required ingredients of a cleaner because of its strong oxidation effect, for example. In addition, water acts as a reducing agent at the high oxidation potential of the potassium permanganate, so that stability problems of the cleaner in aqueous solution result.

It is therefore suggested in AT 408987 that at an oxidizing agent be added to the permanganate, whose oxidation potential exceeds that of the permanganate. Suitable oxidizing agents of this type are, for example, peroxodisulfates, preferably sodium peroxodisulfate. Through the interaction of the permanganate with sodium peroxodisulfate, radical reactions are initiated, as a result of which efficient oxidation of organic substances occurs under highly alkaline conditions, which are achieved by adding alkali hydroxides. In particular, with the cleaning and disinfection agent suggested in AT 408987, implementation in powdered form is possible, which provides advantages in regard to storage and transport.

Furthermore, a color change in the course of the use of the cleaning and disinfection agent described in AT 408987 is described in AT 408987. As will be explained in greater detail, the dominance of a hexavalent manganese species present in the course of the cleaning progress results in a green coloration of the cleaning and disinfection agent, in contrast to the initially violet coloration, which is caused by manganese VII. A yellow coloration of the cleaning and disinfection agent, in contrast, indicates the presence of manganese (II) complexes and therefore also the almost complete consumption of the included oxidizing agent through strong organic impurities.

However, practice has shown that it is advantageous for specific applications to have a cleaning and disinfection agent provided in liquid form. Although a cleaning and disinfection agent according to AT 408987 may be produced and delivered in liquid form, there are possibilities for optimization, in particular in regard to storage life. Furthermore, it has been shown that the addition of an agent for ensuring an alkaline milieu is often not necessary, since alkali hydroxides, alkali carbonates, alkali phosphates, alkali silicates, or alkaline earth hydroxides are usually readily available at industrial customers in particular. Thus, for example, alkali hydroxides, in particular sodium hydroxide, are often used for cleaning commercial and industrial plants or plant components, for example.

In addition, a cleaning and disinfection agent according to AT 408987 has inadequacies in regard to the use of the color change cited as an indicator for the cleaning progress. Applications result in which the cleaning of a facility is performed through typical methods, but a later monitoring of the cleanliness would be of interest, for example. For this purpose, an exploitation of the color change cited would suggest itself, but a cleaning and disinfection agent according to AT 408987 offers possibilities for optimization especially for the application as an agent for monitoring the cleanliness of a plant, for example. Thus, it would be desirable, for example, to add an indicator solution for monitoring the cleaning progress during the circulation of a typically used, highly alkaline cleaning agent, which must be free of organic additives such as surfactants, however, and possibly also detect the cleaning progress quantitatively.

It is therefore the object of the present invention to implement a cleaning, disinfection, and indicator agent which is particularly also suitable for use as an indicator agent for detecting the cleaning progress. This agent is also to be provided in liquid form and be storage-stable.

These objects are achieved by the characterizing features of claim 1.

For this purpose, claim 1 provides a cleaning, disinfection, and indicator agent containing a water-soluble permanganate, in particular for admixture with an agent for ensuring an alkaline milieu having a pH value of at least 11, which is distinguished in that, in addition to the water-soluble permanganate, it comprises a further oxidation agent, whose oxidation potential is above that of manganese VII to manganese VI, pH buffer substances, preferably primary and/or secondary alkali carbonates, as well as oxidation-resistant polyphosphates. With the aid of this formulation it is possible to provide a storage-stable agent in liquid form, which is solely to be combined in the particular application with an agent for ensuring an alkaline milieu such as alkali hydroxides or alkali carbonates. In particular, sodium carbonate and/or sodium hydrogen carbonat come into consideration as the primary and/or secondary alkali carbonates, and the oxidation-resistant polyphosphates result in hardness stabilizers (complexing agents), which are resistant to peroxodisulfates.

The oxidation potential of the further oxidation agent according to claim 2 is preferably above that of $HO_2^-$ to $OH^-$. According to claim 3, the further oxidation agent is a persulfate, preferably a peroxodisulfate, and it is sodium peroxodisulfate according to claim 4. According to claim 5, the permanganate is preferably potassium permanganate.

Different compounds come into consideration as the oxidation-resistant polyphosphates, but in particular sodium tripolyphosphate has been shown to be advantageous according to claim 6 and sodium hexametaphosphate has been shown to be advantageous according to claim 7, a mixture of these two polyphosphates also being usable.

According to claim 8, the following proportional composition of the cleaning, disinfection, and indicator agent according to the present invention is suggested:

3-5% sodium peroxodisulfate, preferably 4%
0.06-0.08% potassium permanganate, preferably 0.07%
5-7% sodium tripolyphosphate, preferably 6%
9-11% sodium hexametaphosphate, preferably 10%

2.0-3.0%, preferably 2.6%, of a mixture of sodium carbonate and sodium hydrogen carbonate, preferably in the ratio 3:1.

The quantities specified relate in this case to an aqueous solution, preferably with the aid of distilled water. Claim 9 suggests a method for cleaning, disinfecting, and monitoring the cleanliness of commercial and industrial plants or plant components, in which, in a first step, the cleaning, disinfection, an indicator agent according to the present invention, comprising a water-soluble permanganate, a further oxidizing agent, whose oxidation potential is above that of manganese VII to manganese VI, pH buffer substances, such as primary and/or secondary alkali carbonates, as well as oxidation-resistant polyphosphates in aqueous solution, is combined with an agent for ensuring an alkaline milieu having a pH value of at least 11, preferably at least 12, in a second step, the solution thus obtained is circulated through the plants or plant components to be cleaned and/or disinfected and the cleaning progress is tracked by ascertaining the intensity of the light emitted in the violet wavelength range by the solution. This method may be referred to as the "batchwise" cleaning method, in which a specific quantity of the cleaning, disinfection, and indicator agent according to the present invention is predefined, which is circulated through the plants and/or plant components to be cleaned. As will be explained in greater detail, in the event of initially contaminated plants, the intensity of the light emitted in the violet wavelength range by the cleaning, disinfection, and indicator solution will first fall, a uniform intensity of a violet coloration of the cleaning, disinfection, and indicator solution indicating a largely clean facility. As will also be explained in greater detail below, the intensity of the light emitted in the green and yellow wavelength ranges by the cleaning, disinfection, and indicator solution will increase in the course of the advancing cleaning process. According to claim 10, the cleaning progress is therefore additionally tracked by ascertaining the intensity of the light emitted by the solution in the green and yellow wavelength ranges.

Of course, after the cleaning method is terminated, water is used for flushing in order to avoid impairment of the subsequent use of the cleaned plant.

In the event of more strongly contaminated plants, the intensity of the light emitted in the violet wavelength range by the cleaning, disinfection, and indicator solution may be reduced so strongly that cleanliness of the plant may not yet be referred to. In this case, it is clearly obvious that primarily the cleaning and disinfection function of the agent according to the present invention is in the foreground. In addition, continuous apportioning of the cleaning, disinfection, and indicator agent according to the present invention recommends itself in these cases, until an essentially uniform violet coloration is achieved. Claim 11 thus provides a method for cleaning, disinfecting, and monitoring the cleanliness of commercial and industrial plants or plant components, in which an aqueous solution having a pH value of at least 11, preferably at least 12, is circulated through the plants or plant components to be cleaned and/or disinfected, and during the circulation a cleaning, disinfection, and indicator agent comprising a water-soluble permanganate, a further oxidizing agent, whose oxidation potential is above that of manganese VII to manganese VI, pH buffer substances, such as primary and/or secondary alkali carbonates, as well as oxidation-resistant polyphosphates is admixed and the cleaning progress is tracked by ascertaining the intensity of the light emitted in the violet wavelength range by the admixed cleaning, disinfection, and indicator agent. The duration of the apportioning of the cleaning, disinfection, and indicator agent according to the present invention may thus be selected depending on the degree of contamination of the plant, until a uniform coloration, which is violet in the ideal case, results. In this case as well, according to claim 12, the cleaning progress may additionally be tracked by ascertaining the intensity of the light emitted in the green and/or yellow wavelength ranges by the admixed cleaning, disinfection, and indicator agent.

Of course, water is again used for flushing after termination of the cleaning method, in order to avoid impairment of the following use of the clean plant.

According to claim 13, the following proportional composition of the cleaning, disinfection, and indicator agent according to the present invention is suggested for the method according to the present invention according to claims 9 and 11:

3-5% sodium peroxodisulfate, preferably 4%
0.06-0.08% potassium permanganate, preferably 0.07%
5-7% sodium tripolyphosphate, preferably 6%
9-11% sodium hexametaphosphate, preferably 10%
2.0-3.0%, preferably 2.6%, of a mixture of sodium carbonate and sodium hydrogen carbonate, preferably in the ratio 3:1.

The quantities specified again relate to an aqueous solution, preferably with the aid of distilled water. Ascertaining the intensity of the light emitted in the violet wavelength range by the admixed cleaning, disinfection, and indicator agent may be performed in different ways. Thus, the ascertainment may be based on a purely visual observation of the coloration. In contrast, according to claim 14, the ascertainment of the light intensity is performed automatically. This may be performed with the aid of spectrophotometers or filter photometers or other suitable light-wavelength-specific detectors, which measure the intensity of the emitted light at specific wavelengths. With the aid of corresponding analysis algorithms, the cleanliness of the plant may be determined on the basis of the data thus measured and subsequent controls of the cleaning process, such as the apportioning of the cleaning, disinfection, and indicator agent according to the present invention, may be performed. A quantitative determination of the degree of cleanliness is thus also advantageous for quality control systems, however, since the time and the measured degree of cleanliness of the plant may be noted in corresponding logs and therefore evidenced.

However, for a comprehensive process judgment, it may also be of interest to calculate the contaminant load removed. This may be performed in particular with automated ascertainment of the intensities of the light emitted in the violet, green, and yellow wavelength ranges, since according to claim 15 the contaminant load removed may be ascertained from the intensity change of the emitted light and the quantity of cleaning, disinfection, and indicator agent supplied.

As already noted, the cleaning and disinfection function of the agent according to the present invention may hardly be separated from its indicator function, since a cleaning and disinfection effect will always occur even with an intended use as an indicator. In fact, however, in plants in which a good degree of cleanliness as already been achieved through preceding cleaning methods, the indicator function may be in the foreground, since the use of the agent according to the present invention hardly has to cause any more cleaning or disinfection. Claim 16 is targeted to these applications, which describes the use of a solution made of a cleaning, disinfection, and indicator agent comprising a water-soluble permanganate, a further oxidizing agent, whose oxidation potential is above that of manganese VII to manganese VI, pH buffer substances, such as primary and/or secondary alkali carbonates, as well as oxidation-resistant polyphosphates and an agent for ensuring an alkali milieu having a pH value of at least 11, preferably at least 12, as an indicator solution for ascertaining the cleanliness of commercial and industrial plants or plant components by ascertaining the intensity of the light emitted in the violet wavelength range by the solution. Furthermore, according to claim 17, in the course of this use the cleanliness of commercial and industrial plants or plant components may additionally be ascertained with the aid of an ascertainment of the intensity of the light emitted in the green and/or yellow wavelength ranges by the solution.

The reactions relevant for the activity of the cleaning, disinfection, and indicator agent according to the present invention will now be described in detail with the aid of a Pourbaix diagram (FIG. 1; for 25° C., 1 bar atmospheric pressure, and an electrolyte activity of 1 mole/l).

Firstly, a strong oxidizing agent is provided in the form and concentration according to the present invention, this preferably being an alkali peroxodisulfate. Although the alkali peroxodisulfate is a strong oxidizing agent, it only reacts slowly with organic compounds at room temperature and in the absence of appropriate catalysts. Rather, the efficient and complete oxidation of organic substances is initiated by the potassium permanganate. Organic carbon is oxidized to oxalate in this case. To accelerate the reaction kinetics between potassium permanganate and organic substances, alkali hydroxides, preferably NaOH, and/or alkali carbonates are added, in order to thus guarantee an alkali milieu.

When the present invention is used, the cleaning, disinfection, and indicator agent is first combined with an agent for ensuring an alkaline milieu having a pH value of at least 11 and water is admixed in suitable dosing. Typically, alkali hydroxides, alkali carbonates, alkali phosphates, alkali silicates, or alkaline earth hydroxides are suitable as agents for ensuring the required alkaline milieu. The hardness stabilizers provided according to the present invention prevent the precipitation of alkaline earth carbonates and hydroxides because of the rising alkalinity of the solution for this purpose, which is decisive at high water hardness in particular. Of course, the water used is to contain no or only very slight quantities of organic substances, since these would impair the indicator function of the cleaning, disinfection, and indicator agent according to the present invention.

When the cleaning, disinfection, and indicator agent is combined with water, hydroxide ions are first oxidized, through the peroxodisulfate (equation 1), but also by the permanganate (equation 2), heptavalent manganese being reduced to manganese having oxidation number +6. Furthermore, oxygen is released.

$$3\ OH^- + S_2O_8^{2-} = HO_2^- + 2\ SO_4^{2-} + H_2O \qquad \text{Equation 1:}$$

$$4\ OH^- + 4\ MnO_4^- = O_2\uparrow + 4\ MnO_4^{2-} + H_2O \qquad \text{Equation 2:}$$

However, the hydrogen peroxide ion resulting upon the oxidation of hydroxide ions by the peroxodisulfate may cause a reoxidation of the manganese (VI) to manganese (VII) (Equation 3):

$$HO_2^- + 2\ MnO_4^{2-} + H_2O = 3\ OH^- + 2\ MnO_4^- \qquad \text{Equation 3:}$$

If the decomposition rate of the peroxodisulfate cannot keep pace with that of the permanganate, because the decomposition of the permanganate is favored by a high concentration and/or good oxidizability of the organic material, for example, increased formation of manganese (VI) will occur. The dominance of the hexavalent manganese species results in a green coloration of the solution, in contrast to the initially violet coloration, which is caused by manganese VII. The oxidation of organic compounds (identified here by "CH$_2$O", which generally stands for carbon of the oxidation stage 0 and especially a carbohydrate) to oxalate by manganese VII and the decomposition of the permanganate accompanying it occurs rapidly, since the high pH value has an anionic effect on numerous organic materials, which makes the attack of anionic oxidation agents easier. The oxidation of organic substances by manganese VII also involves MnO$_4^{3-}$, in which manganese is provided with the oxidation number +5 (Equation 4), but is oxidized again to hexavalent manganese by permanganate (Equation 5).

$$2\ \{CH_2O\} + 3\ MnO_4^- + 2\ H_2O = C_2O_4^{2-} + 3\ MnO_4^{3-} + 8\ H^+ \qquad \text{Equation 4:}$$

$$MnO_4^{3-} + MnO_4^- = 2\ MnO_4^{2-} \qquad \text{Equation 5:}$$

However, the attack of the permanganate on organic substances according to Equation 4 does not cause the high activity of the cleaning, disinfection, and indicator agent according to the present invention. Rather, the rapid and efficient oxidation of organic substances is caused by the radical reactions which now start. The starting point is a SO$_4^-$ radical in this case, which originates from the peroxodisulfate. This radical may first arise through homolytic cleavage of the peroxodisulfate (Equation 6), or through its reaction with organic compounds (Equation 7):

$$S_2O_8^{2-} = 2\ SO_4^- \qquad \text{Equation 6:}$$

$$2\ S_2O_8^{2-} + 2\ \{CH_2O\} + 2H_2O = 2SO_4^{2-} + 2SO_4^- + \{C^{+1}\text{---}R\} + 4H^+ \qquad \text{Equation 7:}$$

In this case, $\{C^{+1}\text{---}R\}$ identifies a radical having carbon in the oxidation stage +1, e.g., formally $\{H_2C_2O_3\}^{2-}$, in which a double bond exists between the carbon atoms. Bolded compounds identify radicals and/or radical ions.

As experimental results have shown, however, the SO$_4^-$ primarily appears to arise through the interaction with existing manganese compounds. It may be assumed that manganese VI and/or manganese V compounds have a radical forming effect on peroxodisulfate according to reactions 8 and 9:

$$MnO_4^{2-} + C_2O_4^{2-} + 2\ H_2O = MnO_4^{3-} + 2\ CO_3^{2-} + 4\ H^+ \qquad \text{Equation 8:}$$

$$MnO_4^{3-} + S_2O_8^{2-} = MnO_4^{2-} + SO_4^{2-} + SO_4^- \qquad \text{Equation 9:}$$

A cascade of radical reactions is now set in motion, of which only the most important may be cited in the following. Thus, the SO$_4^-$ radical causes the formation of OH— radicals (Equation 10). This radical is known to be among the most reactive compounds and oxidizes organic substances (Equation 11), SO$_4^-$ radicals again being able to arise as a further result (Equation 12):

$$SO_4^- + H_2O = HSO_4^- + OH. \qquad \text{Equation 10:}$$

$$2\ OH. + 2\ \{CH_2O\} + H_2O = 2\ OH^- + \{C^{+1}\text{---}R\} + 4\ H^+ \qquad \text{Equation 11:}$$

$$\{C^{+1}\text{---}R\} + 4\ S_2O_8^{2-} + H_2O = 4SO_4^{2-} + 4SO_4^- + C_2O_4^{2-} + 4H^+ \qquad \text{Equation 12:}$$

However, after its formation according to Equation 10, the hydroxide radical may also react with oxalate (Equation 13), the sulfate radical being produced again by peroxodisulfate as a further result (Equation 14):

$$OH. + C_2O_4^{2-} = OH^- + C_2O_4^- \qquad \text{Equation 13:}$$

$$C_2O_4^- + S_2O_8^{2-} = 2\ H_2O = 2\ CO_3^{2-} + SO_4^{2-} + SO_4^- + 4\ H^+ \qquad \text{Equation 14:}$$

Another reaction channel for the oxidation of organic compounds involves the sulfate radical itself. The sulfate radical oxidizes organic compounds (Equation 15) and may finally be resupplied by peroxodisulfate (Equation 16):

$$2\ SO_4^- + 2\ \{CH_2O\} + H_2O = 2\ SO_4^{2-} + \{C^{+1}{-}R\} + 4\ H^+ \quad \text{Equation 15:}$$

$$\{C^{+1}{-}R\} + 4\ S_2O_8^{2-} + H_2O = 4SO_4^{2-} + 4SO_4^- + C_2O_4^{2-} + 4H^+ \quad \text{Equation 16:}$$

The sulfate radical may also react with oxalate (Equation 17), it again being resupplied using a peroxodisulfate molecule (Equation 18):

$$SO_4^- + C_2O_4^{2-} = SO_4^{2-} + C_2O_4^- \quad \text{Equation 17:}$$

$$C_2O_4^- + S_2O_8^{2-} + 2\ H_2O = 2\ CO_3^{2-} + SO_4^{2-} + SO_4^- + 4\ H^+ \quad \text{Equation 18:}$$

It is thus obvious that an efficient oxidation of organic compounds, since it is radically mediated, occurs in the course of the sequence of reactions 10-18, which is initiated by manganese compounds of different oxidation stages and is maintained by peroxodisulfate.

Recombination reactions between radicals finally arrest the chain reactions 10-18 (Equations 19-24):

$$SO_4^- + SO_4^- = S_2O_8^{2-} \quad \text{Equation 19:}$$

$$SO_4^- + OH. = HSO_5^- \text{(unstable)} \quad \text{Equation 20:}$$

$$4\ SO_4^- + \{C^{+1}{-}R\} + H_2O = 4\ SO_4^{2-} + C_2O_4^{2-} + 4\ H^+ \quad \text{Equation 21:}$$

$$OH. + OH. = H_2O_2 \quad \text{Equation 22:}$$

$$4\ OH. + \{C^{+1}{-}R\} + H_2O = 4\ OH^- + C_2O_4^{2-} + 4\ H^+ \quad \text{Equation 23:}$$

$$3\ \{C^{+1}{-}R\} + 3\ H_2O = C_2O_4^{2-} + 4\ \{CH_2O\} + 4\ OH^{-(dis\text{-}proportionation\ of,\ for\ example,\ \{H_2C_2O_3\}^{2-})} \quad \text{Equation 24:}$$

Since manganese (VI) behaves thermodynamically unstably in water, manganese II becomes dominant as a further result (Equation 25):

$$MnO_4^{2-} + H_2O = O_2\uparrow + HMnO_2^- + OH^- \quad \text{Equation 25:}$$

A yellow coloration of the solution indicates the presence of manganese (II), which forms oxalate complexes, and thus also the almost complete termination of the cleaning and disinfection process.

Oxygen and hydrogen peroxide are released during the entire sequence of the chain reactions 10-25 (Equations 1, 2, 16, 25), which additionally supports the cleaning and disinfection process. Peroxodisulfate compounds do not have to be used exclusively as an additional, strong oxidizing agent. Other oxidizing agents, whose oxidation potential is above that of manganese VII to manganese VI (line $MnO_4^-/MnO_4^-$ in the Pourbaix diagram of FIG. 1), preferably above that of $HO_2^-$ to $OH^-$ (line $HO_2^-/OH^-$ in the Pourbaix diagram of FIG. 1), come into consideration for this purpose. Periodate would also be suitable, for example, for this purpose in regard to the line $MnO_4^-/MnO_4^-$, which ensures reactivation of manganese V and/or VI to permanganate in the scope of a somewhat modified chemistry. Potassium monopersulfate (triple salt) may be used as a substitute for peroxodisulfate. The use of peroxodiphosphate and ozone is theoretically conceivable, but may hardly be implemented technically. Peroxodiphosphate is currently not available in large quantities and ozone decomposes very rapidly because of its high reactivity, because of which it appears unsuitable for commercial cleaning, disinfection, and indicator agents. Hypochlorite would be sufficiently stable in aqueous solution, but the electrochemical dominance of the redox pair $ClO^-/Cl^-$ is also to sure to form $HO_2^-$ ions in the event of long-term storage.

The application of the cleaning, disinfection, and indicator agent according to the present invention may be performed as a "batchwise" cleaning method, in which a specific quantity of the cleaning, disinfection, and indicator agent according to the present invention is predefined, which is circulated through the plants and/or plant components to be cleaned. For this purpose, a suitable quantity of water is admixed with 0.5-1.5% of the cleaning, disinfection, and indicator agent according to the present invention, thoroughly mixed, and subsequently brought to a pH value of at least 11, preferably at least 12 with the aid of addition of alkali hydroxides, alkali carbonates, alkali phosphates, alkali silicates, and/or alkaline earth hydroxides. Of course, existing apparatus for cleaning the plants, such as CIP ("cleaning in place") facilities may be used for this purpose. The solution thus obtained is circulated in the plant as a further result, the return flowage and/or even the entire volume being judged at the end of the evaluation using color comparison and/or photometric measurement. With initially contaminated plants, the intensity of the light emitted in the violet wavelength range by the cleaning, disinfection, and indicator solution will first fall, and the intensity of the light emitted in the green and yellow wavelength ranges by the cleaning, disinfection, and indicator solution will increase. The stronger the color of the pure-violet starting color, the stronger was the contamination of the entire system. In the event of strong contamination, cleaning using a new amount of cleaning, disinfection, and indicator solution and subsequently renewed evaluation are to be repeated. A uniform intensity of a violet coloration of the cleaning, disinfection, and indicator solution indicates an almost completely clean plant. The color of the return flowage of the cleaning, disinfection, and indicator solution will be a mixture of violet and green in this case, significant green components also being able to be contained in this case. In this case, the cleaning is to be repeated with the aid of a new quantity of cleaning, disinfection, and indicator solution.

The intensity of the light emitted in the violet wavelength range by the admixed cleaning, disinfection, and indicator agent may be ascertained in different ways. Thus, the ascertainment may be based on the purely visual observation of the coloration. However, the light intensity is preferably ascertained automatically. This may be performed with the aid of spectrophotometers or filter photometers or other suitable light-wavelength-specific detectors, which measure the intensity of the emitted light at specific wavelengths. With the aid of corresponding analysis algorithms, the cleanliness of the plant may be determined on the basis of the data thus measured and subsequent controls of the cleaning process, such as the apportioning of the cleaning, disinfection, and indicator agent according to the present invention, may be performed. However, quantitative determination of the degree of cleanliness is also advantageous for quality control systems, since the time and the measured degree of cleanliness of the plant may be noted in corresponding logs and thus evidenced.

However, for a comprehensive process judgment, it may also be of interest to calculate the contaminant load removed. This may be performed in particular with automated ascertainment of the intensities of the light emitted in the violet, green, and yellow wavelength ranges, since the contaminant load removed may be ascertained from the intensity change of the emitted light and the quantity of cleaning, disinfection, and indicator agent supplied. Of course, water is used for flushing after termination of the cleaning method in order to avoid impairment of the following use of the cleaned plant.

In contrast to "batchwise" (discontinuous) cleaning methods, in many cases continuous apportioning of the cleaning, disinfection, and indicator agent may also be indicated until a uniform violet coloration is achieved. Such a procedure is recommended in particular in the event of strongly contaminated plants. For this purpose, for example, an alkaline starting solution is provided in a tank from which a flow through the plant may be produced. During the circulation of this alkaline starting solution through the plant, the cleaning, disinfection, and indicator agent according to the present invention is admixed to the starting solution flowing out, until the desired (mixed) color value has been reached in the return flowage to the tank.

In methods of this type, the cleaning and disinfection function of the cleaning, disinfection, and indicator agent according to the present invention is primarily in the foreground. Depending on the degree of contamination of the plant, the duration of the dosing of the cleaning, disinfection, and indicator agent according to the present invention may be selected until a uniform violet coloration results. In this case as well, the cleaning progress may additionally be tracked by ascertaining the intensity of the light emitted in the green and/or yellow wavelength ranges by the admixed cleaning, disinfection, and indicator agent. The color value may again be ascertained with the aid of visual observation or mechanically and automatically with the aid of photometric in-line measurements.

Of course, water is again used for flushing after termination of the cleaning method in order to avoid impairment of the following use of the cleaned plant.

All components of the cleaning, disinfection, and indicator agent according to the present invention are provided in liquid form, the combination with alkaline agents and water which occurs only shortly before the application being extremely advantageous for the storage stability of the agent according to the present invention.

The following examples are to document the manifold nature of the possible uses of the cleaning, disinfection, and indicator agent according to the present invention and are not to be understood in a restrictive sense.

EXAMPLE 1

The carbonators and fillers of the filling plant of a mineral water producer are to be monitored for their cleanliness with the aid of the cleaning, disinfection, and indicator agent according to the present invention. The cleaning is typically performed in a CIP loop with the aid of a 2% formic acid solution and a subsequent disinfection with the aid of a 0.1% peracetic acid. Typically, there is no alkaline cleaning. The cleanliness of the facility is typically monitored only in regard to the completeness of the peracetic flushing via evaluation of the pH value, the acid capacity, and/or the conductivity of the flushing liquid, preferably water.

However, before the cleanliness of the plant is monitored, a comparatively clean plant may first be assumed, so that the agent according to the present invention is to be used above all as an indicator. This means that exploitation of the cleaning and disinfecting action of the agent is not primarily desired, but rather solely its indicator action. For this purpose, a volume of 6000 l of water is prepared in a tank (e.g., in the CIP tank) in the meaning of a "batchwise" (discontinuous) method. The dead volume of the plant to be checked is 4000 l. Directly before beginning the circulation, the cleaning, disinfection, and indicator agent according to the present invention is admixed in a concentration of 1%. Subsequently, a concentration of 0.50% is set with the aid of the lye (NaOH) available at mineral water producers, which corresponds to a pH value of the solution of above 12.5. The temperature of the solution is 54° C. and its color is violet.

The solution thus obtained is now circulated for 25 minutes through the plant to be checked in a first cleaning step. After ending the circulation, the indicator liquid according to the present invention has a yellow-green color, which corresponds approximately to a 50:50 ratio of manganese VI to manganese II. The mobilized contaminant load is calculated at 80-120 g (as $\{CH_2O\}$). The plant has thus been shown to be contaminated to an unexpected extent, so that in spite of the actually intended mere indication of the degree of cleanliness of the plant, the agent according to the present invention has also unfolded its cleaning and disinfecting action.

Since because of the yellowish color, cleanliness of the plant may not yet be discussed, 1% of the agent according to the present invention is again added to the tank. A wine-red mixed coloration of the solution thus results. After a further 12 minutes of circulation of the solution to the plant, the color remains almost completely unchanged, however, so that one may refer to termination of the cleaning process and the plant may actually also be referred to as clean.

EXAMPLE 2

The wort path in the brewhouse of a brewery, which comprises, inter alia, a plate heat exchanger, is to be cleaned with the aid of the cleaning, disinfection, and indicator agent according to the present invention and monitored for its cleanliness. The cleaning is typically performed up to three times a day in a CIP loop with the aid of a 3-4% NaOH solution having a phosphoric acid surfactant additive in a quantity below 0.5%. The temperature is approximately 80-85° C. for this purpose. The cleaning solution is accumulated, slurried, and alkalized with lye via conductivity measurements. Typically, there is no acidic postcleaning, but rather, if necessary neutralization using $CO_2$ and disinfection using steam. The cleanliness of the plant is typically monitored only in regard to the completeness of the flushing of the cleaning solution by evaluating the pH value, the acid capacity, and/or the conductivity of the flushing liquid, preferably water.

In this case, a comparatively contaminated plant must be assumed, so that the agent according to the present invention will primarily unfold its cleaning function. For this purpose, in the meaning of a continuous method, a volume of 6500 l water is prepared in a tank (e.g., in the CIP tank). The dead volume of the plant to be checked is 5000 l. With the aid of the lye (NaOH) available at the brewery, a concentration of 1.50% is set, which corresponds to a pH value of the solution of at least 13.0. The alkaline starting solution thus obtained is circulated through the plant components to be cleaned.

During the circulation of this starting solution (temperature 60° C), the cleaning, disinfection, and indicator agent according to the present invention is admixed in the solution flowing out. During a circulation duration of 80 minutes, 200 l is thus admixed (3.0%). The color of the cleaning solution achieved after the circulation is deep yellow and contains several hundreds of milligrams per liter of brown turbidity-causing solids. The mobilized contaminant load was calculated at 20-30 kg (as $\{CH_2O\}$). Tendencies toward green/yellow-green could be observed again and again during the addition and/or circulation of the cleaning solution through the plant. With increasing concentration of the cleaning, disinfection, and indicator agent according to the present invention, the color of the return flowage changed again and again to pure yellow through mobilization of new dirt deposits.

In this case, a thorough chemical cleaning of the plant and/or disassembly of the plant and the heat exchanger with subsequent mechanical cleaning is recommended After com-

The invention claimed is:

1. An agent comprising:
a first oxidant comprising a water-soluble permanganate,
a second oxidant whose oxidation potential exceeds that of a mixture containing 50 mol % manganese VII and 50 mol % manganese VI; and
a primary and/or secondary alkali carbonate,
wherein the agent is in a liquid form and is storage-stable, and
wherein concentrations of ingredients are such that the agent is pH buffered and storage-stable in liquid form.

2. The agent according to claim 1, wherein the oxidation potential of the second oxidant is above that of $HO_2^-$ to $OH^-$.

3. The agent according to claim 1, wherein the second oxidant comprises a persulfate.

4. The agent according to claim 3, wherein the second oxidant comprises a peroxodisulfate.

5. The agent according to claim 4, wherein the peroxodisulfate comprises sodium peroxodisulfate.

6. The agent according to claim 1, wherein the permanganate comprises potassium permanganate.

7. The agent according to claim 1, wherein the agent comprises sodiumtripolyphosphate.

8. The agent according to claim 1, wherein the agent is in a liquid form and storage-stable.

9. The composition of claim 1, wherein the composition changes color on contact with the substance external to the composition, wherein said color change allows a visual evaluation of an amount of the substance external to the composition oxidized by the composition.

10. The composition as claimed in claim 1, wherein the color change is from purple to a second color other than purple.

11. The composition as claimed in claim 10, wherein the second color is green.

12. The composition as claimed in claim 10, wherein the second color is yellow.

13. The composition as claimed in claim 1, wherein the composition changes color upon contact with a substance external to the composition, wherein the substance external to the composition comprises an organic substance.

14. The composition of claim 13, wherein the water-soluble permanganate reacts with the organic substance.

15. The composition of claim 13, wherein a peroxodisulfate reacts with the organic substance.

16. The composition as claimed in claim 1, wherein the composition changes color upon contact with a substance external to the composition, wherein the substance external to the composition comprises an organic substance, the second oxidant comprises peroxodisulfate, and both the water-soluble permanganate and the peroxodisulfate react with the organic substance.

17. The composition as claimed in claim 1, wherein the agent comprises: a peroxodisulfate, a polyphosphate, a metaphosphate, and a carbonate.

18. The agent according to claim 1, wherein the agent contains sodium hexametaphosphate.

19. The agent according to claim 1, wherein the agent comprises the following composition:
3-5% sodiumperoxodisulfate,
0.06-0.08% potassium permanganate,
5-7% sodium tripolyphosphate,
9-11% sodium hexametaphosphate,
2.0-3.0%, of the mixture of sodium carbonate and sodium hydrogen carbonate.

20. A method for cleaning, disinfection, and monitoring cleanliness, comprising: combining the agent of claim 1 with water to form a first aqueous solution;
combining an alkaline agent with the first aqueous solution to form a second aqueous solution, wherein the alkaline agent is configured to ensure a pH of the second aqueous solution of at least 11;
and
tracking the cleaning progress by monitoring an intensity of light passed through the second aqueous solution.

21. The method according to claim 20, wherein the light comprises violet, green and/or yellow wavelength.

22. The method according to claim 20, further comprising circulating the second aqueous solution through the components to be cleaned and/or disinfected.

23. The method according to claim 20, wherein the agent comprises the following composition:
3-5% sodium peroxodisulfate,
0.06-0.08% potassium permanganate,
5-7% sodium tripolyphosphate,
9-11% sodium hexametaphosphate,
2.0-3 0%, of a mixture of sodium carbonate and sodium hydrogen carbonate.

24. The method according to claim 20, wherein the monitoring the intensity of the light is ascertained automatically.

25. The method according to claim 20, wherein the cleanliness is calculated from the intensity change of the light passed through the second aqueous solution and the quantity of the agent used.

26. The method according to claim 20 further comprising circulating the alkaline agent through the components to be cleaned and/or disinfected and subsequently combining the alkaline agent with the first aqueous solution.

27. The method of claim 20, wherein the method is configured to clean carbonators, fillers or brewery.

28. The method of claim 20, wherein the second aqueous solution is in a form ready for use in cleaning a surface in a plant.

29. An agent comprising:
a first oxidant comprising a water-soluble permanganate,
a second oxidant whose oxidation potential exceeds that of a mixture containing 50 mol % manganese VII and 50 mol % manganese VI; and
a pH buffer,
wherein the agent is in a liquid form and is storage-stable, and
wherein concentrations of ingredients are such that the agent is pH buffered and storage-stable in liquid form.

30. The agent of claim 29, wherein the pH buffer comprises an alkali.

31. The agent of claim 30, wherein the alkali comprises a primary and/or secondary alkali carbonate.

32. The agent of claim 29, further comprising a hardness stabilizer.

33. An aqueous solution comprising an agent, the agent comprising:
a first oxidant comprising a water-soluble permanganate,
a second oxidant whose oxidation potential exceeds that of a mixture containing 50 mol % manganese VII and 50 mol % manganese VI; and
a pH buffer,
wherein the agent is in a liquid form and is storage-stable, and
wherein concentrations of ingredients are such that the agent is pH buffered and storage-stable in liquid form.

34. The aqueous solution of claim 33, wherein the pH buffer comprises an alkali.

35. The aqueous solution of claim 34, wherein the alkali comprises a primary and/or secondary alkali carbonate.

36. The aqueous solution of claim 33, further comprising an alkaline agent, wherein the alkaline agent is configured to ensure a pH of the aqueous solution of at least 11.

37. The aqueous solution of claim 33, further comprising an alkaline agent, wherein the alkaline agent is configured to ensure a pH of the aqueous solution of at least 12.

38. The agent of claim 37, wherein the hardness stabilizer comprises a polyphosphate.

39. The aqueous solution of claim 33, further comprising a hardness stabilizer.

40. The aqueous solution of claim 39, wherein the hardness stabilizer comprises a polyphosphate.

41. The aqueous solution of claim 33, wherein the aqueous solution is ready for use in cleaning a surface in a plant.

42. The aqueous solution of claim 36, wherein the aqueous solution is ready for use in cleaning a surface in a plant.

* * * * *